United States Patent
Karavas et al.

(10) Patent No.: US 9,849,147 B2
(45) Date of Patent: Dec. 26, 2017

(54) PHARMACEUTICAL COMPOSITION CONTAINING PHOSPHATE BINDING POLYMER

(75) Inventors: Evangelos Karavas, Pallini Attikis (GR); Efthimios Koutris, Pallini Attikis (GR); Vasiliki Samara, Pallini Attikis (GR); Analia Diakidou, Pallini Attikis (GR); Georgia Papanikolaou, Pallini Attikis (GR); Panagiotis Mparmpalexis, Pallini Attikis (GR)

(73) Assignee: PHARMATHEN S.A., Pallini, Attikis (GR)

( * ) Notice: Subject to any disclaimer, the term of this patent is extended or adjusted under 35 U.S.C. 154(b) by 0 days.

(21) Appl. No.: 14/408,053

(22) PCT Filed: Jun. 15, 2012

(86) PCT No.: PCT/EP2012/002547
§ 371 (c)(1),
(2), (4) Date: Dec. 15, 2014

(87) PCT Pub. No.: WO2013/185789
PCT Pub. Date: Dec. 19, 2013

(65) Prior Publication Data
US 2015/0182555 A1    Jul. 2, 2015

(51) Int. Cl.
*A61K 31/785* (2006.01)
*A61K 9/00* (2006.01)
*A61K 9/20* (2006.01)

(52) U.S. Cl.
CPC .......... *A61K 31/785* (2013.01); *A61K 9/0056* (2013.01); *A61K 9/2027* (2013.01)

(58) Field of Classification Search
CPC ... A61K 31/785; A61K 9/0056; A61K 9/2027
See application file for complete search history.

(56) References Cited

U.S. PATENT DOCUMENTS

| | | | |
|---|---|---|---|
| 2007/0190020 A1 | 8/2007 | Hrakovsky et al. | |
| 2008/0234337 A1* | 9/2008 | Kuwahara | A61K 31/00 514/365 |
| 2009/0232885 A1* | 9/2009 | Venkatesh | A61K 9/1617 424/455 |
| 2009/0280178 A1* | 11/2009 | Hedge | A61K 9/284 424/474 |
| 2010/0092421 A1 | 4/2010 | Hedge et al. | |
| 2011/0129530 A1* | 6/2011 | Venkatesh | A61K 9/0056 424/470 |

FOREIGN PATENT DOCUMENTS

| | | | |
|---|---|---|---|
| CA | 2642255 A1 | 8/2007 | |
| CA | 2661987 A1 | 5/2008 | |
| CA | 2749074 A1 | 5/2008 | |
| EP | 2441779 A1 | 4/2012 | |
| WO | 2007094779 A1 | 8/2007 | |
| WO | 2008062437 A2 | 5/2008 | |
| WO | 2009034540 A1 | 3/2009 | |
| WO | WO2009/034540 * | 3/2009 | ............. A61K 9/00 |
| WO | 2011135591 A2 | 11/2011 | |

* cited by examiner

*Primary Examiner* — Sean M Basquill
(74) *Attorney, Agent, or Firm* — AKC Patents, LLC; Aliki K. Collins

(57) ABSTRACT

The present invention relates to a fast dissolving tablet comprising a therapeutically effective amount of a phosphate binding polymer, such as sevelamer or pharmaceutically acceptable salt or derivative thereof, that exhibit limited swelling in the oral cavity, has pleasant taste and mouth feel, high phosphate binding capacity with fast binding kinetics and require limited amount of water intake. A process for the preparation thereof is disclosed.

6 Claims, 2 Drawing Sheets

PHARMACEUTICAL COMPOSITION CONTAINING PHOSPHATE BINDING POLYMER

TECHNICAL FIELD OF THE INVENTION

The present invention relates to an oral solid dosage form and particularly a fast dissolving tablet comprising a therapeutically effective amount of phosphate binding polymer such as sevelamer or pharmaceutical acceptable salts or derivatives thereof, that exhibit limited swelling in the oral cavity, has pleasant taste and mouth feel, high phosphate binding capacity with fast binding kinetics and requires limited amount of water intake. A method for the preparation thereof is also provided.

BACKGROUND OF THE INVENTION

Patients undergoing hemodialysis result in hyperphosphatemia. This can cause secondary hyperparathyroidism and promotes vascular calcification. To avoid these complications, serum phosphate (Pi) levels must be controlled by phosphate binders. Phosphate binders are a group of medications used to reduce the absorption of phosphates. It has been suggested that the sequestering of dietary phosphates in the stomach before they enter the small intestine and undergo absorption would be a beneficial attribute for a phosphate binder. There has been a progressive evolution of oral phosphate binders from aluminium, through calcium salts and on to newer agents such as sevelamer and lanthanum carbonate which are all dosed, on average, three times per day.

The three key elements in the management of elevated serum phosphate in CKD are: i) dietary phosphate restriction, ii) removal of phosphate from the systemic circulation by dialysis (hemodialysis) or peritoneal dialysis and iii) the use of phosphate binding agents to impede absorption of dietary phosphate from the GI tract (i.e., oral phosphate binders). Dietary phosphate restriction is impractical for many patients and it can be restricted only to a certain extent without risking protein malnutrition, particularly in elderly patients. Conventional 4-h, thrice-weekly hemodialysis removes approximately 1000 mg of phosphate per session, but this is generally insufficient to maintain phosphate levels within the recommended targets. Peritoneal dialysis removes slightly more than this when averaged over a week, but is still insufficient. Moreover, cost and patient acceptance issues further limit the usage of these modalities. Thus, around 90% of dialysis patients continue to need oral phosphate binders in an effort to control their phosphate levels.

In general, the ideal characteristics of an oral phosphate binder include: i) high affinity for binding phosphate which means low required dose (pill burden), ii) rapid phosphate binding regardless of ambient pH, iii) low solubility, iv) little to no systemic absorption, v) non-toxic and without side-effects, vi) solid oral dosage form, vii) palatability which encourages patient's compliance and viii) low cost.

Sevelamer is a polymeric amine that binds phosphate and is administered orally. It's a polyallylamine crosslinked with epichlorohydrin in which approximately forty percent of the amines are protonated. Sevelamer is hydrophilic and it exists as a hydrogel that can absorb approximately twenty times its weight in water, but is insoluble in most solvents including water.

Sevelamer main salt forms are the hydrochloride and the carbonate. Sevelamer hydrochloride was the first synthetic non-aluminum and calcium-free phosphate binder to become commercially available. It is an anion exchange resin consisting of a non-absorbed poly (allylamine hydrochloride) polymer. It contains multiple amines separated by one carbon from the polymer backbone. These amines become partially protonated in the intestine and interact with phosphate and other ions through ionic and hydrogen bonding. A more recent formulation of sevelamer consisting of sevelamer carbonate has been approved for use. This alternative sevelamer form appears to have equivalent ability to lower phosphorus serum concentration with that of sevelamer hydrochloride without affecting the serum bicarbonate concentration.

Sevelamer, unlike other phosphate binders, is able to correct hyperphosphatemia without promoting arterial calcification. A significant point to be noted is that end-stage renal disease patients restrict their fluid intake in order to control blood pressure and avoid heart failure. Furthermore, phosphate binders, due to their nature and their functionality are administrated in large doses several times per day. The size of the marketed tablets is large enough to prohibit their use by many patient categories such as elderly people and children, who could have difficulties swallowing them.

The most frequently used method for administering an active pharmaceutical ingredient to a patient are solid oral pharmaceutical dosage forms. Widely used oral medications are tablets and capsules. Nevertheless, many individuals have difficulties in swallowing. Elderly patients and children are usually unwilling, or unable, to swallow tablets and capsules. This leads to poor compliance and ineffective treatment of the patient. Additionally, such dosage forms are inconvenient for people that do not have access to water or a fluid.

In order to overcome said drawbacks and to improve compliance, lozenges, chewable, orally dispersible and sublingual dosage forms have been introduced. Some of the challenges in developing such dosage forms include taste-masking, mouth-feel, grittiness and manufacturing issues. Furthermore, packaging can be a critical aspect since they have to maintain low moisture content during storage. Another typical problem is their low hardness and, as a result, their inadequate friability causing inconvenience during the manufacturing and packaging procedure. Furthermore, a significant issue is the hydroscopicity of many of those products mainly due to the hydroscopicity of the active ingredients used.

However, until now, a fast dissolving composition in the above mentioned tablet forms comprising sevelamer or salts or derivatives thereof as the active pharmaceutical ingredient has not been proposed, probably because of its high hydroscopicity, bitter taste and swelling in the oral cavity, causing difficulties in manufacture and increase discomfort to patients leading to reduces compliance.

Various compositions and methods for preparing chewable tablets of various active ingredients have been proposed.

U.S. Pat. No. 7,029,699 B1 provide a chewable tablet containing Acetaminophen, a water-disintegratable and compressible carbohydrate and a binder.

U.S. Pat. No. 7,482,022 B1 discloses a palatable, chewable tablet comprising Cetirizine, a sweetener, a combination of a grape and vanilla flavouring and a cyclodextrin.

U.S. Pat. No. 5,629,013 B1 claims a chewable composition of calcium carbonate with aspartame, saccharin and 3-1-menthoxypropane-1,2-diol.

WO 95/05165 A1 discloses chewable tablets comprising hydrolysed gelatine as a flavour enhancer.

Therefore, there exists the need of a composition that will provide better patient compliance and ease of administration, comprising a phosphate binder such as sevelamer or salts or derivatives thereof as the active ingredient.

SUMMARY OF THE INVENTION

An object of the present invention is to provide a fast dissolving composition, containing a phosphate binder, such as sevelamer or pharmaceutically acceptable salts or derivatives thereof, as the active pharmaceutical ingredient that is easy to manufacture and has adequate pharmacotechnical properties.

Another object of the present invention is to provide a fast dissolving composition for oral administration containing a phosphate binder and in particular sevelamer or pharmaceutical acceptable salts or derivatives thereof as an active ingredient that has good mouth-feel, no swelling in the oral cavity, pleasant taste and enhanced chewing properties.

In accordance with the above mentioned objectives of the present invention, a fast dissolving composition for oral administration is provided comprising a phosphate binder, in particular sevelamer or pharmaceutical acceptable salts or derivatives thereof, and an effective amount of at least one pharmaceutically acceptable excipient having hydrogen bond acceptor groups or being able to form a coating over the said active ingredient in order to minimize its swelling properties. The excipient may be selected from diluents, fillers, waxes, gelling and non-gelling agents, binders, plasticizers, solubilizing agents, wetting agents, suspending agents, flavour enhancers, emulsifying agents The composition prepared according to the present invention disintegrates rapidly, does not swell in the oral cavity, has a pleasant taste with high phosphate binding capacity and fast binding kinetics.

An object of the present invention is to provide a process for the preparation of a fast dissolving composition of a phosphate binder and in particular of sevelamer or pharmaceutical acceptable salts or derivatives thereof, comprising:
mixing the total quantity of the pharmaceutical active ingredient with appropriate amounts of at least one pharmaceutical excipient having hydrogen bond acceptor groups, until a homogeneous mixture is achieved;
adding a pharmaceutically acceptable granulation liquid, such as ethanol, methanol, acetone, isopropyl alcohol, water or a mixture thereof in order to create a well wetted mass;
drying the wetted mass and sieving;
forming a homogenous mixture of the above mixture with at least one pharmaceutically acceptable excipient, such as binders, disintegrants, flavour enhancers or glidants;
adding a lubricant and mixing until uniform;
formulating the resulting mixture in a solid dosage form by compressing it into the desired tablet form.

Alternatively, a process for the preparation of a fast dissolving composition of a phosphate binder and in particular of sevelamer or pharmaceutical acceptable salts or derivatives thereof according to the present invention comprises:
forming a homogeneous mixture of the total quantity of the pharmaceutical active ingredient with appropriate amounts of at least one pharmaceutical excipient, such as waxes, fillers, binders, disintegrants and optionally one or more plasticizers by melt mixing;
mixing the total quantity of the above mixture after cooling to room temperature, with appropriate amounts of one or more pharmaceutical excipient, such as binders, fillers, disintegrants or viscosity increasing agents, until a homogeneous mixture is achieved;
dispersing or dissolving an appropriate amount of suitable pharmaceutical excipient, capable in effectively coating the API, in a pharmaceutically acceptable granulation liquid, such as ethanol, methanol, acetone, isopropyl alcohol, water etc.,
adding the above dispersion/solution to the melt mixed powder/granule in order to create a well wetted mass;
drying the wetted mass and sieving;
forming a homogenous mixture of the above mixture with at least one pharmaceutically acceptable excipient, such as binders, disintegrants, flavour enhancers and/or glidants;
adding at least one lubricant and mixing until uniform;
formulating the resulting mixture in a solid dosage form by compressing it into the desired tablet form.

The active pharmaceutical ingredient optionally can be hydrated partially or totally in order to minimize it's swelling during manufacturing process and storage.

Other objects and advantages of the present invention will become apparent to those skilled in the art in view of the following detailed description.

DETAILED DESCRIPTION OF THE INVENTION

Figure 1:
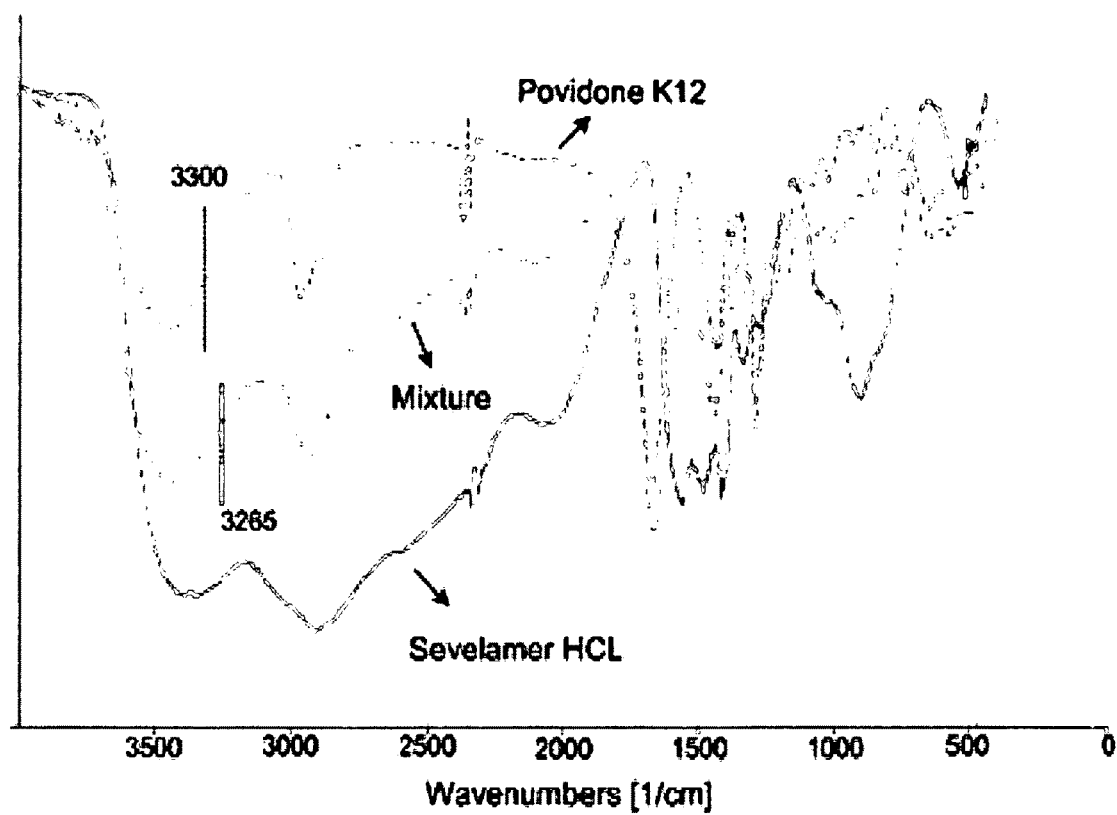
FIG. 1: FTIR spectra of sevelamer HCl, povidone K12 and mixture of both after wet granulation.

A major objective of the present invention is to provide a fast dissolving composition for oral administration containing a phosphate binder and in particular sevelamer or pharmaceutical acceptable salts or derivatives thereof, as the active pharmaceutical ingredient.

An optimum fast dissolving composition of sevelamer or pharmaceutical acceptable salts or derivatives thereof, should exhibit limited swelling in the oral cavity, while having pleasant taste and mouth feel, fast disintegrating properties, high phosphate binding capacity with fast binding kinetics and require limited amount of water intake.

According to the present invention a fast dissolving and/or fast disintegrating composition is a pharmaceutical dosage form that dissolves and/or disintegrates in the oral cavity quickly after administration. The active pharmaceutical ingredient is released from such compositions immediately in the mouth. Such dosage forms are tablets orally dispersible, chewable, sublingual, lozenges and the like and is well known that are different from typical dosage forms such as immediate release film coated or sustained release tablets that need to be swallowed by the patient in order to initiate release of the active substance in the stomach. The manufacture of tablets orally dispersible, chewable, sublingual, lozenges and the like is easily interchangeable and well within the knowledge of a person skill in the art of pharmaceutical technology.

One of the main problems regarding sevelamer, its pharmaceutically acceptable salts (especially the HCl salt) or derivatives thereof is the fact that they swell rapidly when in contact with liquids, making them significantly difficult to handle and swallow.

According to the present invention, swelling suppression of the active substance can be achieved with the use of pharmaceutically acceptable excipients that are able to form bonds with the amine groups of the polymer. Those excipients have appropriate reactive groups that can participate in interactions (ionic, hydrogen bonding or Van der Waals) with the active ingredients reactive groups. In the case of sevelamer polymer and its pharmaceutically acceptable salts, reactive groups capable of forming hydrogen bonds with the amine groups of the active substance include excipients with hydrogen acceptor groups, such as —C=O, —C—O—C— and the like. Examples of suitable excipients include, but not limited to, fillers, waxes, gelling and non-gelling agents, binders, plasticizers, coating agents, solubilizing agents, wetting agents, suspending agents, viscosity increasing agents, such as povidone (PVP), crospovidone, polyethylene-glycol (PEG), cellulose based excipient (such as HPMC, SCMC HPC etc.) polymethacrylate co-polymers (Eudragit), chitosan and others.

The above interaction is reversible and the dissociation takes place relatively rapidly under physiological pH values, and hence high phosphate binding capacity with fast binding kinetics is achieved. During the dissociation, the amine groups of sevelamer become again partially protonated and interact with phosphate and other ions through ionic and hydrogen bonding.

Alternatively, according to the present invention swelling suppression can be achieved by forming a coating over the active substance granules. Several excipients such as waxes, fillers, gelling and non-gelling agents, binders, plasticizers, solubilizing agents, wetting agents, suspending agents, viscosity increasing agents and others can be used for this purpose. In this case the coating acts as a physical barrier to the drug particles, thereby minimizing the active substance contact with mouth saliva, leading to reduced swelling, and reduced interaction with taste buds. Coating of the active substance may be achieved by several techniques such as melt mixing, wet granulation, spray coating, fluidized bed, air suspension coating, micro-encapsulation, solvent evaporation or combination thereof.

Optionally, swelling may be further suppressed during product formulation and storage by hydrating the active pharmaceutical ingredient with water before starting the production process. This procedure ensures that the active ingredient will not further swell during the manufacturing process and that the finished dosage form will not swell and change size during storage.

In a preferred embodiment, the present invention provides a fast disintegrating lozenge, chewable, orally dispersible or sublingual tablet comprising sevelamer or its pharmaceutically acceptable salts or derivatives as the active pharmaceutical ingredient, one or more binders with hydrogen bond acceptor groups such as polyvinylpyrrolidone in an amount of from 5% to 30% wt, a diluent providing a pleasant sweet taste and cooling sensation such as mannitol, sorbitol and/or dextrate, a disintegrant such as crospovidone or primogel, one or more flavouring/sweetening agents such as menthol, lemon, sucralose and/or vanilla and a lubricant such as magnesium stearate.

Polyvinylpyrrolidone is generally used as tablet binder, coating agent, disintegrant, dissolution enhancer and suspending agent. According to the present invention it can also be used as an "anti-swelling" agent by forming hydrogen bonds with the amino groups of sevelamer. This interaction is reversible and the dissociation takes place relatively rapidly under physiological pH values.

Sevelamer's hydrogen bonding with povidone was investigated with FTIR analysis (FIG. 1). FTIR spectra of sevelamer HCl, povidone K12 and the mixture of both after wet granulation were obtained after appropriate background subtraction in the region of 400 to 4000 cm$^{-1}$. 32 scans over the selected wavenumber range at a resolution of 4 cm$^{-1}$ were averaged for each sample.

The shift of the shoulder/peak of amino groups of sevelamer to lower wevanumbers (3265 cm$^{-1}$) shown in FIG. 1, indicates hydrogen bonding between these groups and the carbonyl groups of PVP.

The fast disintegrating tablet of the present invention comprising sevelamer or its pharmaceutically acceptable salts or derivatives may be alternatively produced by coating the active pharmaceutical ingredient with one or more waxes (stearic acid, carnauba wax, compritol and glyceryl mono stearate) with the aid of melt mixing, further coated with a binder or diluent (ethyl cellulose) using wet granulation. Additionally, diluents which provide a pleasant sweet taste and cooling sensation (mannitol, sorbitol or dextrates), disintegrants (crospovidone or primogel), flavouring/sweetening agents (menthol, lemon, sucralose, vanilla) and lubricants (magnesium stearate) are used. The coating of the active ingredient granules comprises 3% to 25% wt of the total weight of the tablet.

Melt mixing comprises dissolving or dispersing the API in the melted excipients, or heating the homogeneous physical mixture of them, followed by cooling and pulverizing the obtained product. The whole process can be applied using several techniques, such as thermostatic mixers, hot melt extruders etc., while the cooling step can be conducted in several ways such as simple agitation in room temperature or ice bath, stainless steel thin layer spreading followed by a cold draught, spreading on plates placed over dry ice, immersion in liquid nitrogen and others. It is important to state that according to the present invention, increased temperatures during melt mixing do not cause API's instability, such as thermal degradation, oxidation, reduce in bicarbonate anion concentration (in the case of sevelamer carbonate) etc., and do not alter the high phosphate binding capacity and fast binding kinetics of the final product. Wet granulation, although primary intended to impact flowability and compressibility, under certain conditions it was proved to be a useful approach for coating sevelamer drug particles.

Mannitol is used as a diluent as well as a sweet-tasting bodying and texturing agent. Crystalline mannitol, and especially spray-dried mannitol exhibits very low hydroscopicity, making it useful in products that are unstable at high humidity. It prevents moisture absorption from the air, exhibits excellent mechanical compressing properties, has adequate compatibility with the active pharmaceutical ingredient and its sweet, cool taste masks the unpleasant taste of many active pharmaceutical ingredients. Sorbitol has good tabletting properties and increases the tablet strength. Additionally, sorbitol of "instant" quality that is manufactured by spray-drying has even better properties. Dextrates are directly compressible tablet diluents used widely. They are highly water-soluble, give a cool and smooth mouth feel, while they have good taste masking and flavour carrying capacity.

Another object of the present invention is to provide a fast disintegrating composition containing a phosphate binder as an active pharmaceutical ingredient, such as sevelamer or salt or derivatives thereof, which has adequate pharmacotechnical properties such as good flowability, compressibility and fast disintegration.

An important parameter to be considered is the flowability of the tablet, which is presented as a measure of the Carr Index. A Carr index greater than 25% is considered to be an indication of poor flowability, and below 15%, of good flowability. The composition according to the present invention has a Carr Index of 15-25.

The crushing strength and the friability are important and should not change during the storage period. If the crushing strength becomes too high it is difficult for the patient to chew the tablets, if it is too low, the tablet breaks or disintegrates. If the friability is too high, the tablets are fragile. In accordance with the present invention the tablets have a crushing strength of about 40-200 N and this changes at the most 1-2% during the storage period, while friability varies from less than 1% up to 8%. The disintegration time of tablets of the present invention, is less than 5 min, preferably less than 1.5-2 min.

A further object of the present invention is to provide a pharmaceutical dosage formulation for oral administration containing a phosphate binder, in particular sevelamer or pharmaceutical acceptable salts or derivatives thereof, as an active pharmaceutical ingredient that has good mouth-feel, pleasant taste and adequate chewing properties.

Mouth feel of the pharmaceutical composition means that the composition, as long as is in the mouth, has a smooth and minimum unpleasant grittiness, sandy or chalky feeling. Tablets prepared in accordance with the present invention have adequate mouth feel, chewing properties and a pleasant taste.

Another embodiment according to the present invention, is to provide a process for the preparation of a fast dissolving composition for oral administration of a phosphate binder, in particular sevelamer or pharmaceutical acceptable salts or derivatives thereof, as the active pharmaceutical ingredient and an effective amount of at least one excipient with hydrogen bond acceptor groups, which is able to reduce swelling in the oral cavity. Said process comprises:

mixing the total quantity of the pharmaceutical ingredient with appropriate amounts of at least one pharmaceutical excipient with hydrogen bond acceptor groups, until a homogeneous mixture is achieved;

adding a pharmaceutically acceptable granulation liquid, such as ethanol, methanol, acetone, iso propyl alcohol, water or a mixtures thereof in order to create a well wetted mass;

drying the wetted mass and sieving;

forming a homogenous mixture of the above mixture with at least one pharmaceutically acceptable excipient, such as binders, disintegrants, flavour enhancers, glidants and the like;

optionally, processing the formed mixture by dry granulation, slugging, roller compacting, milling or sieving, or combinations thereof;

adding a lubricant and mixing until uniform;

formulating the resulting mixture in a solid dosage form by compressing it into the desired tablet form.

Alternatively the process for the preparation of a fast dissolving composition for oral administration of a phosphate binder, in particular sevelamer or pharmaceutical acceptable salts thereof, as the active pharmaceutical ingredient comprises an appropriate amount of at least one excipient which is able to effectively coat the API and hence reduce swelling in the oral cavity and improve mouth feel and taste. Said alternative process comprises the following steps:

forming a homogeneous mixture of the total quantity of the said pharmaceutical ingredient with appropriate amounts of at least one pharmaceutical excipient, such as waxes, fillers, binders, disintegrants and optionally one or more plasticizers by melt mixing;

optionally, mixing the total quantity of the above mixture after cooling to room temperature, with appropriate amounts of one or more pharmaceutical excipient, such as coating agents, binders, fillers, disintegrants, suspending agents, gelling and non-gelling agents, viscosity increasing agents and the like, until a homogeneous mixture is achieved;

dispersing or dissolving an appropriate amount of suitable pharmaceutical excipient, capable in effectively coating the API, in a pharmaceutically acceptable granulation liquid, such as ethanol, methanol, acetone, iso propyl alcohol, water or mixtures thereof;

adding the above dispersion/solution to the melt mixed powder/granule in order to create a well wetted mass;

drying the wetted mass and sieving;

forming a homogenous mixture of the above granule/powder mixture with at least one pharmaceutically acceptable excipient, such as binders, disintegrants, flavour enhancers and/or glidants;

adding at least one lubricant and mixing until uniform;

formulating the resulting mixture in a solid dosage form by compressing it into the desired tablet form.

The process according to the present invention comprises optionally hydrating a part or the total quantity of the said active pharmaceutical ingredient.

The pharmaceutical compositions of the present invention may also contain one or more additional formulation ingredients selected from a wide variety of excipients. According to the desired properties of the composition, any number of ingredients may be selected, alone or in combination, based upon their known uses in preparation of solid dosage form compositions. Such ingredients include, but are not limited to, diluents, binders, glidants, compression aids, waxes, gelling and non-gelling agents, viscosity increasing agents, solubilizing agents, disintegrants, lubricants, flavours, water scavengers, colorants, sweetener, coating agents, preservatives.

These optional excipients should be compatible with the active substance so that they do not cause instability to the composition. Non-limiting examples of excipients that can be used according the present invention are: Diluents, for example, calcium carbonate, calcium phosphate dibasic, calcium phosphate tribasic, calcium sulfate, microcrystalline cellulose (MCC), microcrystalline silicified cellulose, powdered cellulose, dextrates, dextrose, fructose, lactitol, lactose anhydrous, lactose monohydrate, lactose dihydrate, lactose trihydrate, mannitol sorbitol, starch, pregelatinized starch, sucrose, talc, xylitol, maltose, maltodextrin and maltitol.

Disintegrants can be chosen by the group of microcrystalline cellulose, croscarmellose sodium, crosslinked polyvinylpyrrolidone, sodium starch glycolate, pregelatinized starch and low substituted hydroxy propyl cellulose (HPC).

Suitable flavouring or sweetening agent(s) used in the composition may include but are not limited to strawberry, cherry, peppermint, black currant, caramel, aspartame, saccharin, sucralose, vanilla, lemon, menthol, sucrose and fructose.

Lubricants that may be used are talc, sodium stearyl fumarate, calcium stearate, magnesium stearate, zinc stearate, glyceryl behenate, stearic acid and glyceryl monostearate. Anti-adherents and glidants that can optionally be used are talc, magnesium silicate, calcium silicate and colloidal, or amorphous, silicon dioxide and the like.

The following examples illustrate preferred embodiments in accordance with the present invention without intending to limit the scope or spirit of the invention.

EXAMPLES

Example 1

TABLE 1

Tablet composition of example 1

| Ingredients | mg per tablet | % of total weight |
|---|---|---|
| Sevelamer HCl | 800 | 34.8 |
| Povidone K12 | 320 | 13.9 |
| Dextrose | 1100 | 47.8 |
| Saccharine | 60 | 2.6 |
| Aerosil | 10 | 0.4 |
| Mg-Stearate | 10 | 0.4 |
| Total | 2300 | 100 |

Tablets of the above formulations were prepared according to the following manufacturing process: sevelamer HCl and povidone K12 were sieved and admixed together. The resulting mixture was wet granulated with ethanol until a well wetted mass was obtained. After sieving and drying, dextrose, saccharin and aerosol were added and admixed until a homogeneous mixture was obtained. Magnesium stearate was finally added and admixed and the resulting mixture was compressed into the desirable tablet form.

The tablets had satisfactory pharmacotechnical properties. The bulk mixture exhibited satisfactory flow, while disintegration time, friability and hardness were well within specifications.

Example 2

TABLE 2

Tablet composition of example 2

| Ingredients | mg per tablet | % of total weight |
|---|---|---|
| Sevelamer HCl | 800 | 32.3 |
| Povidone K12 | 320 | 12.9 |
| Povidone VA64 | 180 | 7.3 |
| Dextrose | 1100 | 44.4 |
| Saccharine | 60 | 2.4 |
| Aerosil | 10 | 0.4 |
| Mg-Stearate | 10 | 0.4 |
| Total | 2480 | 100 |

Tablets of the above formulations were prepared according to the following manufacturing process: sevelamer HCl, povidone K12 and povidone VA64, were sieved and admixed together. The resulting mixture was wet granulated with ethanol until a well wetted mass was obtained. After sieving and drying dextrose, saccharin and aerosol were added and admixed until a homogeneous mixture was obtained. Magnesium stearate was finally added and admixed and the resulting mixture was compressed into the desirable tablet form.

The tablets had satisfactory pharmacotechnical properties. The bulk mixture exhibited satisfactory flow, while disintegration time, friability and hardness were well within specifications.

The formulations of examples 1 & 2 do not swell in the oral cavity, thus are easier to swallow. This is attributed to the formation of hydrogen bonding between the selected excipient(s) and the active pharmaceutical ingredient.

The effect of the hydrogen bonding on the phosphate binding capacity and kinetics was evaluated in vitro. The appropriate binding studies were performed. In particular, Langmuir binding constants $k_1$ (affinity constant) and $k_2$ (capacity constant) were determined within the linear binding range of the resins, at pH 4.0 and pH 7.0, with and without acid pre-treatment, at different phosphate concentrations ranging from 1 mM to 40 mM. For the in vitro kinetic binding study, conducted at pH 4.0 and pH 7.0, two phosphate concentrations of 1 mM and 40 mM were prepared and tested samples were collected at pre-determined time intervals. Incubation parameters, analytical testing and calculation procedures were conducted.

The phosphate binding capacity and kinetics of the fast disintegrating formulations of examples 1 and 2 were compared with the marketed film coated orally administrable tablet formulations of sevelamer HCl. The results presented in table 3 below indicate that the tested formulations exhibited equivalent phosphate binding properties to the marketed product of sevelamer HCl.

TABLE 3

Comparative phosphate binding results of chewable tablets of examples 1 and 2 with the marketed sevelamer HCl product at pH 7.0 without acid pre-treatment.

| Formulation | Affinity constant, $k_1$ (mmole$^{-1}$) | Binding capacity, $k_2$ (mmole/g) |
|---|---|---|
| Example 1 | 0.54 | 6.54 |
| Example 2 | 0.52 | 7.09 |
| Marketed | 0.65 | 6.58 |

The results of in vitro binding kinetics conducted at pH 4.0 and 7.0 for 1 mM and 40 mM phosphate concentrations with and without acid pre-treatment were all comparable to the marketed formulation of sevelamer HCl.

The bound phosphate concentration was calculated by subtracting the unbound concentration from the initial concentration (i.e., 40.0, 30.0, 14.5, 10.0, 7.5, 5.0, 2.5 and 1.0 mM) as follows:

Bound phosphate conc.(mM)=Initial conc.−unbound phosphate conc.(mM)

The phosphate binding capacity was then expressed in mmol of phosphate/g of polymer, Phosphate binding capacity (mmol/g)=bound phosphate conc.(mM)*Vs/weight (g); where, Vs: Volume of solution; Weight (g): Weight of the product.

Langmuir binding affinity constants ($k_1$) and capacity constant ($k_2$) were calculated by performing linear regression on a plot of the unbound (mM)/bound (mmol/g) fraction versus the unbound (mM) concentration. $k_1$ and $k_2$ constants were derived from the plot by applying the following equations: $k_1$=Slope (a)/Intercept (c) & $k_2$=1/Slope (a).

The hydrogen bond formation between the amino groups of the API and the carbonyl groups of povidone, reduced the swelling in the mouth cavity and did not interfere with the phosphate capacity or kinetics of the API. The formulations of examples 1 and 2 are easy to take, have a good taste and mouth feel, adequate chewing properties with no swelling in the oral cavity, exhibit high phosphate binding capacity with fast binding kinetics and require limited amount of water intake.

Example 3

TABLE 4

Tablet composition of example 3

| Ingredients | mg per tablet | % of total weight |
|---|---|---|
| Sevelamer carbonate | 800 | 39.9 |
| HPMC phthalate | 90 | 4.5 |
| Eudragit E100 | 90 | 4.5 |
| Crospovidone | 200 | 10.0 |
| Mannitol | 800 | 39.9 |
| Sucralose | 5 | 0.2 |
| Menthol | 8 | 0.4 |
| Vanilla | 4 | 0.2 |
| Mg-Stearate | 10 | 0.5 |
| Total | 1997 | 100.0 |

Tablets of the above formulation were prepared according to the following manufacturing process: Sevelamer carbonate was wet granulated firstly with an acetone solution of HPMC phthalate and then with an ethanolic solution of Eudragit E100 until a well wetted mass was obtained. After drying and sieving, crospovidone and mannitol were sieved and admixed until a homogeneous mixture was obtained. Sucralose, menthol, vanilla and magnesium stearate were then sieved and admixed with the prepared bulk. The resulting mixture was compressed into the desirable tablet form.

The tablets had satisfactory pharmacotechnical properties. The bulk mixture exhibited satisfactory flow, while disintegration time, friability and hardness were well within specifications. Forming a coating on sevelamer with HPMC phthalate and Eudragit E100 eliminated API's swelling in the oral cavity when chewing, while mannitol, menthol, sucralose and vanilla improved mouth-feel and enhanced the taste of the final product.

Example 4

TABLE 5

Chewable tablet composition of example 4

| Formulations | mg per tablet | % of total weight |
|---|---|---|
| Sevelamer carbonate | 800 | 39.8 |
| Glyceryl monostearate | 300 | 14.9 |
| Crospovidone | 200 | 9.9 |
| Mannitol | 684 | 34.0 |
| Sucralose | 5 | 0.2 |
| Menthol | 8 | 0.4 |
| Vanilla | 4 | 0.2 |
| Mg-Stearate | 10 | 0.5 |
| Total | 2011 | 100.0 |

Tablets of the above formulation were prepared according to the following manufacturing process: sevelamer carbonate and glyceryl monostearate were melt mixed until a homogenous mixture was obtained. The mixture was cooled to room temperature and sieved. Crospovidone and mannitol were sieved, added to the mixture of sevelamer and admixed until a homogeneous mixture was obtained. Finally, sucralose, menthol, vanilla and magnesium stearate were sieved and admixed with the prepared bulk. The resulting mixture was compressed into the desirable tablet form.

The tablets had satisfactory pharmacotechnical properties. The bulk mixture exhibited satisfactory flow, while disintegration time, friability and hardness were well within specifications. Coating sevemaler with glyceryl monostearate after melt mixing eliminated API's swelling in the oral cavity when chewing, while mannitol, menthol, sucralose and vanilla improved mouth-feel and enhanced the taste of the final product.

All applied conditions during melt mixing (temperature and time of mixing, shear forces applied etc.) did not cause degradation to the API (thermal instability, oxidation etc.) or altered its bicarbonate anion concentration.

Example 5

TABLE 6

Tablet composition of example 5

| Ingredients | mg per tablet | % of total weight |
|---|---|---|
| Sevelamer carbonate | 800 | 38.6 |
| Stearic acid | 20 | 1.0 |
| Carnauba wax | 47 | 2.3 |
| Glyceryl behenate | 22 | 1.1 |
| Glyceryl monostearate | 137 | 6.6 |
| Ethyl cellulose | 137 | 6.6 |
| Crospovidone | 200 | 9.6 |
| Mannitol | 684 | 33.0 |
| Sucralose | 5 | 0.2 |
| Menthol | 8 | 0.4 |
| Vanilla | 4 | 0.2 |
| Mg-stearate | 10 | 0.5 |
| Total | 2074 | 100.0 |

Tablets of the above formulation were prepared according to the following manufacturing process: sevelamer carbonate and stearic acid, carnauba wax, glyceryl behenate and glyceryl monostearate were melt mixed until a homogenous mixture was obtained. The mixture was cooled to room temperature, sieved and wet granulated with an ethanolic suspension of ethyl cellulose until a well wetted mass was obtained. After drying and sieving, crospovidone and mannitol were admixed until a homogeneous mixture was obtained. Finally, sucralose, menthol, vanilla and magnesium stearate were sieved and admixed with the prepared bulk. The resulting mixture was compressed into the desirable tablet form.

The tablets had satisfactory pharmacotechnical properties. The bulk mixture exhibited satisfactory flow, while disintegration time, friability and hardness were well within specifications. Coating of sevelamer carbonate using both techniques (melt mixing and wet granulation) reduced further API's swelling in the oral cavity when chewing, while mannitol, menthol, sucralose and vanilla mouth-feel and enhanced the taste of the final product.

All applied conditions during melt mixing (temperature and time of mixing, shear forces applied etc.) did not cause degradation to the API (thermal instability, oxidation etc.) or altered its bicarbonate anion concentration.

The phosphate binding capacity and kinetics of formulation of example 5 was compared with the marketed film coated orally administrable tablet formulations of sevelamer carbonate. The results presented in table 7 below indicate that the tested formulation exhibited equivalent phosphate binding properties to the marketed product of sevelamer carbonate.

TABLE 7

Comparative phosphate binding results of chewable tablets of examples 5 with the marketed sevelamer carbonate product at pH 7.0 without acid pre-treatment.

| Formulation | Affinity constant, $k_1$ (mmole$^{-1}$) | Binding capacity, $k_2$ (mmole/g) |
|---|---|---|
| Example 5 | 0.69 | 5.06 |
| Marketed formulation | 0.67 | 5.51 |

The results of in vitro binding kinetics conducted at pH 4.0 and 7.0 for 1 mM and 40 mM phosphate concentrations with and without acid pre-treatment were all comparable to the mar marketed formulation of sevelamer carbonate.

Formation of a coating on the API by both methods (melt mixing and wet granulation), reduced the swelling in the mouth cavity and did not interfere with the phosphate capacity or kinetics of the API. The formulation of example 5 is easy to take, have a good taste and mouth feel, adequate chewing properties with no swelling in the oral cavity, exhibit high phosphate binding capacity with fast binding kinetics and require limited amount of water intake.

Figure 2:
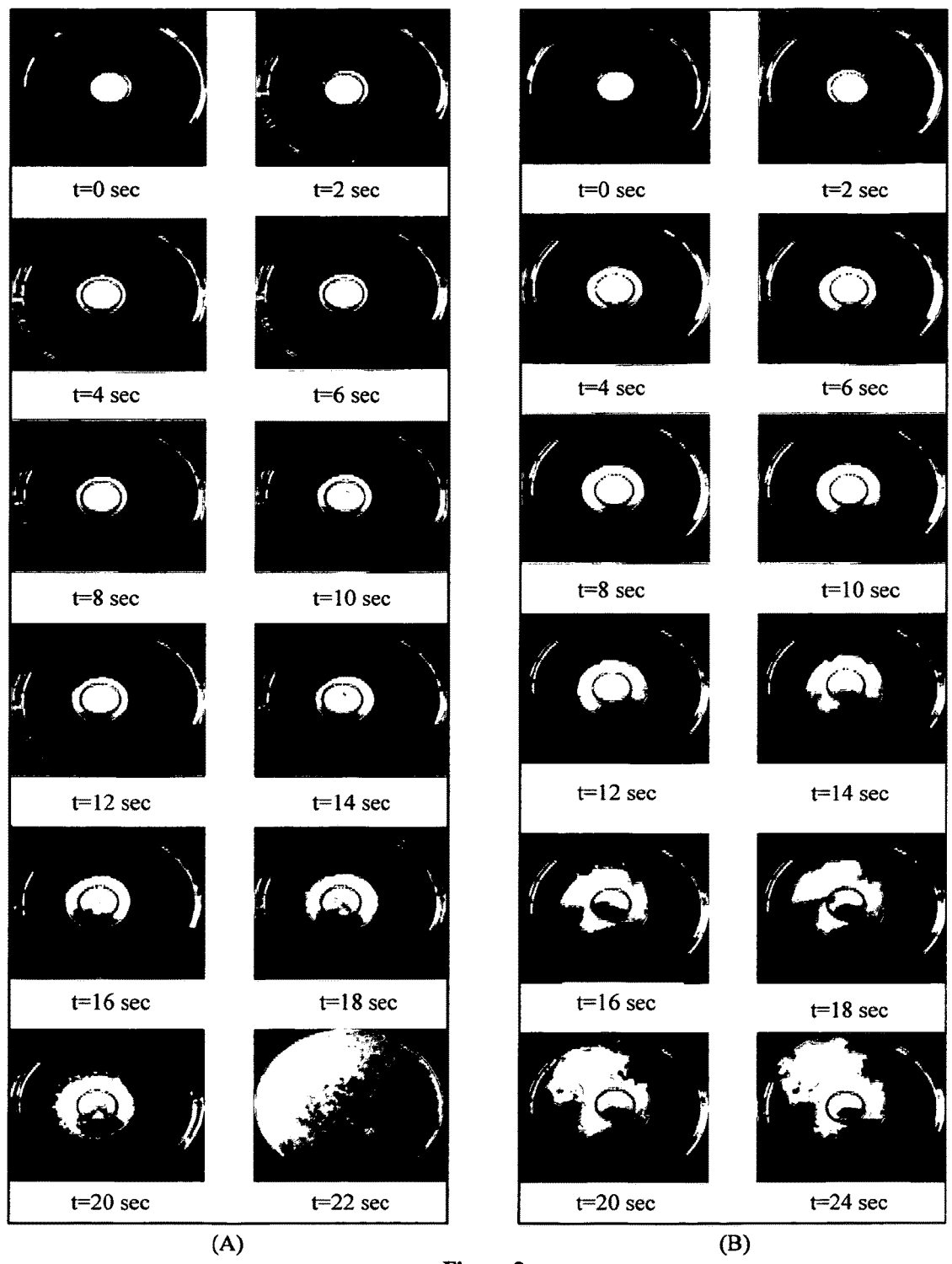
FIG. 2: In vitro swelling study of formulation of example 5 (A) and marketed product (B). The circle depicts the initial size of tablets.

In order to verify the reduced swelling ability, chewable tablets of example 5 and of the marketed sevelamer product, were placed in petri-disks and 40 ml of phosphate buffer saline pH 7.4 was added. Photos were taken from time zero to 22 seconds in two second intervals (FIG. 2). As it is obvious from FIG. 2, the tablets of marketed sevelamer product (FIG. 2B) underwent greater and faster swelling compared to those of example 5 (FIG. 2A). Tablet of example 5 was easily dispersed in few seconds (FIG. 2A, t=22 sec), in contrary to the marketed sevelamer tablet that extensive swelling continued for several minutes.

While the present invention has been described with respect to the preferred embodiments, it will be apparent to those skilled in the art that various changes and modifications may be made in the invention without departing from the spirit and scope thereof, as defined in the appended claims.

The invention claimed is:

1. A pharmaceutical composition comprising:
   sevelamer or a pharmaceutically acceptable salt or derivative thereof, as the active ingredient;
   a pharmaceutically acceptable excipient, wherein the pharmaceutically acceptable excipient comprises at least one of carnauba wax, glyceryl behenate, glyceryl monostearate, or mixtures thereof;
   wherein the pharmaceutically acceptable excipient forms a homogeneous mixture with the active ingredient via melt mixing and in the homogeneous mixture the pharmaceutically acceptable excipient bonds directly to the active ingredient and forms hydrogen bonds with amine groups of the active ingredient, thereby reducing swelling of the active ingredient in an oral cavity;
   wherein the pharmaceutical composition comprises a tablet that is orally dispersible, chewable, sublingual, or lozenges;
   wherein the pharmaceutically acceptable excipient comprises an amount of at least 3% of the total weight of the tablet; and
   wherein the pharmaceutical composition dissolves or disintegrates in the oral cavity releasing the active ingredient in the oral cavity in less than 5 minutes.

2. The pharmaceutical composition according to claim 1, wherein the pharmaceutically acceptable excipient that reduces swelling of the active ingredient in the oral cavity comprises an amount from 3% to 30% wt of the total weight of the tablet.

3. The pharmaceutical composition according to claim 1, wherein the pharmaceutical composition further comprises a diluent configured to provide a pleasant sweet taste and cooling sensation, a disintegrant, one or more flavouring/sweetening agents, a glidant and a lubricant.

4. The pharmaceutical composition according to claim 3, wherein the diluent comprises one of ethyl cellulose, mannitol, sorbitol and/or dextrate, wherein the disintegrant comprises crospovidone or sodium starch glycolate, wherein the one or more flavouring/sweetening agents comprise one of menthol, lemon, sucralose and/or vanilla, wherein the glidant comprises talc or colloidal silicon dioxide and wherein the lubricant comprises magnesium stearate.

5. A pharmaceutical composition comprising:
   sevelamer or a pharmaceutically acceptable salt or derivative thereof, as the active ingredient;
   a coating formed over granules of the active ingredient, wherein the coating comprises a pharmaceutically acceptable excipient that comprises at least one of carnauba wax, glyceryl behenate, glyceryl monostearate, or mixtures thereof;
   wherein the pharmaceutically acceptable excipient forms a homogeneous mixture with the active ingredient via melt mixing and in the homogeneous mixture the pharmaceutically acceptable excipient bonds directly to the active ingredient and forms hydrogen bonds with amine groups of the active ingredient, thereby reducing swelling of the active ingredient in an oral cavity;
   wherein the pharmaceutical composition comprises a tablet that is orally dispersible, chewable, sublingual, or lozenges; and
   wherein the pharmaceutical composition dissolves or disintegrates in the oral cavity releasing the active ingredient in the oral cavity in less than 5 minutes.

6. The pharmaceutical composition according to claim 5, wherein the coating comprises at least 3% of the total weight of the tablet.

* * * * *